United States Patent

Pyatnitskaya et al.

[11] 4,144,348
[45] Mar. 13, 1979

[54] MEDICAL PREPARATION FOR TREATMENT OF ALCOHOLISM

[76] Inventors: Irina N. Pyatnitskaya, 3 Peschanaya, 5, kv. 267, Moscow; Vladimir I. Ivanov, ulitsa Scherbakova, 4, kv. 37, Mytischi Moskovskoi oblasti; Nina K. Borovkova, ulitsa Guryanova, 51, kv. 188; Nina G. Naidenova, ulitsa Kamchatskaya, 2, korpus 1, kv. 26, both of Moscow, all of U.S.S.R.

[21] Appl. No.: 827,344

[22] Filed: Aug. 24, 1977

[30] Foreign Application Priority Data

Oct. 29, 1976 [SU] U.S.S.R. .................. 2412834 (I)

[51] Int. Cl.² .................................. A61K 31/40
[52] U.S. Cl. .................................. 424/274
[58] Field of Search .......................... 424/274

*Primary Examiner*—Donald B. Moyer
*Attorney, Agent, or Firm*—Burgess, Ryan and Wayne

[57] ABSTRACT

A composition for the treatment of alcoholism, comprising as the active ingredient: ω-(3'-phenylpyrrolidyl-1')-6-propionyl benzo-1,4-dioxan hydrochloride of the following formula

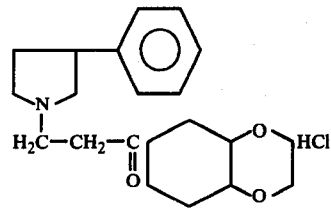

and a suitable pharmaceutical carrier.

The composition is used for the treatment of alcoholism at any stage in the development of the disease. The preparation has low toxicity, has no side effects and is not habit forming.

8 Claims, No Drawings

MEDICAL PREPARATION FOR TREATMENT OF ALCOHOLISM

1. Field of the Invention

This invention relates to psychiatry, and more particularly to a new composition for the treatment of alcoholism at any stage in the development of the disease.

During the initial stage in the development of alcoholism, when the patient is still communicative, trusts the physician and seeks recovery, the instant composition can be used for out-patient treatment, but in other cases of alcoholism, particularly at the stage of encephalopathy, hospitalization is initially required for a short period of time with subsequent follow-up observation and additional out-patient treatment.

The composition is a novel one and has not been described in the literature.

2. Brief Description of the Invention

A new composition, according to the invention, for the treatment of alcoholism comprises as the active ingredient: ω -(3'-phenylpyrrolidyl-1')-6 -propionyl benzo-1,4-dioxan hydrochloride, of the following formula:

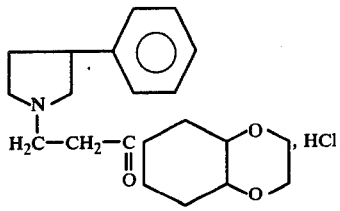

in combination with a pharmaceutically acceptable carrier.

When preparing tablets, it is most desirable to use as the carrier a filler selected from the group consisting of sodium chloride, starch, saccharose and lactose.

Each tablet should preferably contain 0.015 or 0.030 g of said active ingredient, which facilitates the optimal selection of single and daily doses.

When preparing an injectable solution it is advisable to use as the pharmaceutical carrier 0.01–0.001 N solution of hydrogen chloride and apyrogenic distilled water, which is the best solvent of ω-(3'-phenylpyrrolidyl-1')-6 -propionyl benzo-1,4-dioxan hydrochloride.

The concentration of said active ingredient in the injectable solution should preferably be within 1.0 to 1.5% by weight.

The methods for treating alcoholism will be described below in greater detail in conjunction with the process and results of clinical trials.

DETAILED DESCRIPTION OF THE INVENTION

The proposed preparation differs advantageously from prior art remedies for alcoholism.

For example as compared to preparations of tetraethylthiuram disulfide (better known under the names: Antabuse, Teruram, Espiral) and tetraethylthiuram disulfide types which, when alcohol is taken, cause vascular and other disregulatory vegetative reactions threatening the patient's life, the present composition does not rule out the use of alcoholic beverages, since it does not cause any complications endangering life. However, the taste and smell of alcohol undergo changes, the state of euphoria does not set in due to the practically complete suppression of psychic symptoms of intoxication and, correspondingly, no desire to continue drinking is observed either on the day of taking alcoholic beverages or later. Since the present composition does not lead to conflict between the craving for alcohol and the fear of using it, as is the case with the above-mentioned preparations, no depression occurs, and rejection of treatment is extremely rare. In distinction from the above-mentioned preparations, the present composition does not cause any undesirable side effects (headache, somnolence) either in the beginning or at the end of treatment. Attention must also be drawn to the moral depreciation of Antabuse among alcoholics because of its widely known antagonists (sour foods, such as lemons).

Compared to preparations causing an emetic reaction in the case of drinking alcohol (Apomorphine, Emetine), the present composition differs advantageously in that it has no contraindications for use in cases of diseases of the alimentary tract, vascular pathologies and traumatic lesions of the brain. Besides, a single course of treatment according to the present invention ensures abstinence from alcohol for a period from 1.0 to 1.5 years, whereas the conditioned aversional reflex is rapidly extinguished.

The present composition has been subjected to clinical trials.

Two hundred patients (male) without any special selection (group 1) were subjected to treatment for chronic alcoholism with the present composition. Another two hundred patients (male) treated for alcoholism with Antabuse (group 2), and two hundred patients (male) treated with Apomorphine (group 3) served as controls. Information about the patients in groups 2 and 3 (controls) and the effectiveness of their treatment were derived from their case histories and by collecting the catamnesis during repeated admission to the clinical hospital. Control grous 2 and 3 were selected so that there would be similarity of the basic controlled indices during treatment between all the contingents of patients (groups 1, 2 and 3).

The patients in each of the three groups were subdivided into three sub-groups depending on the gravity of the disease. The establishment of the stage of alcoholism and, correspondingly, the sub-grouping of patients were carried out according to the following symptom-complexes; for stage 1:

(a) altered reactivity syndrome: disappearance of vomiting as a protective symptom in cases of overdosage of alcohol, systematic alcoholization accompanied by rising tolerance to alcohol and palimpsests (partial amnesias) of intoxication.

(b) the syndrome of psychic dependence on alcohol, manifested in the need for the mental comfort of intoxication and an obsessive longing for alcohol; for stage 2:

(a) altered reactivity syndrome: loss of the protective vomiting reflex, maximum tolerance, loss of control over the quantity of used alcoholic drinks, pseudo-dipsomania, intoxication accompanied by the effect of stimulation and amnesias ("blackout").

(b) the syndrome of physical dependence on alcohol: the state of physical comfort during intoxication, abstinence syndrome, compulsive crave for alcohol;

(c) complications: acute psychosis (with the syndrome of disorders of consciousness), descent of personality and somato-neurological pathology; for stage 3:

(a) altered reactivity syndrome manifested in lower tolerance, true dipsomania and amnesias induced by small quantities of alcohol;

(b) syndrome of physical dependence on alcohol: compulsive crave and abstinence syndrome;

(c) complications: alcoholic encephalopathy, loss of situational control as an indicator of deterioration of intellect, protracted forms of psychoses, energy exhaustion and somato-neurological incapacity.

The comparability of the results of the clinical examination of the test and control groups is substantiated by the data given in Tables 1, 2, 3.

The distribution of patients according to groups and stages of alcoholism is reflected in Table 1.

Table 1.

| Groups of patients | Groups of Patients and Stages of Alcoholism | | | |
|---|---|---|---|---|
| | Number of patients distributed according to stages | | | |
| | 1 | 2 | 3 | Total |
| 1 | 2 | 3 | 4 | 5 |
| 1. Present composition | 8 | 132 | 60 | 200 |
| 2. Antabuse | 8 | 132 | 60 | 200 |
| 3. Apomorphine | 4 | 134 | 62 | 200 |
| Total: | 20 | 398 | 182 | 600 |

The minimum number of patients of the first stage of alcoholism is due to the fact that in this period patients very seldom appeal for medical treatment on their own accord, since they to not consider themselves to be sick and refuse treatment. For this reason, the patients in the clinical hospital with the first stage of alcoholism are those who were admitted on the insistence of their relatives.

The age distribution of the patients of the above-mentioned groups is shown in Table 2.

Table 2.

| Groups of patients | Characteristics of the Patients | | | | | | | |
|---|---|---|---|---|---|---|---|---|
| | Number of patients according to age (years) | | | | | | | |
| | 19–20 | 21–25 | 26–30 | 36–40 | 41–45 | 46–50 | 51–56 | Total |
| 1 | 2 | 3 | 4 | 5 | 6 | 7 | 8 | 9 |
| 1. Present composition | 11 | 23 | 40 | 51 | 47 | 19 | 9 | 200 |
| 2. Antabuse | 7 | 20 | 44 | 49 | 46 | 22 | 12 | 200 |
| 3. Apomorphine | 12 | 23 | 39 | 52 | 49 | 18 | 7 | 200 |
| Total: | 30 | 66 | 123 | 152 | 142 | 59 | 28 | 600 |

As to the duration of the disease, the groups were approximately equal (see Table 3).

Table 3

| Groups of patients | Duration of Alcoholism | | | | | |
|---|---|---|---|---|---|---|
| | Number of patients according to duration of disease (years) | | | | | |
| | 2–5 | 6–10 | 11–15 | 16–20 | 21–25 | Total |
| 1 | 2 | 3 | 4 | 5 | 6 | 7 |
| 1. Present composition | 32 | 70 | 51 | 37 | 10 | 200 |
| 2. Antabuse | 30 | 70 | 54 | 37 | 9 | 200 |
| 3. Apomorphine | 32 | 72 | 53 | 35 | 8 | 200 |
| Total: | 94 | 192 | 158 | 109 | 27 | 600 |

Treatment with the present composition consisted in the following, in the first, test group. Patients, irrespective of accompanying pathologies of the cardio-vascular and alimentary systems and the liver (since no contra-indications for the use of the composition have been revealed), were prescribed 0.030 to 0.040 g of the preparation orally 3 times a day, with the intake of tablets being supervised, or with 2 to 3 ml of a 1% solution 3 times a day in the form of intramuscular injections. The form of administration was selected with due account for the personality of the patient (injections are preferable for patients at the 2nd and 3rd stages). The sizes of the single and daily doses were selected according to the degree in which the symptoms of the disease were manifest. However, in all cases, the daily dose did not exceed 0.180 g in tablets or 0.120 g in injections. A course of such treatment lasted 2 to 3 weeks. Subsequently the patients received the present composition for another 2 to 3 months 1 to 2 times a week in tablets (under supervision) in two 0.030 to 0.040 g doses on the days of administration.

As a result of clinical trials, which lasted 4.5 years (54 months), the following was established:

In distinction from the remedies known in the art, the present composition removes and suppresses the craving for alcohol, including the removal of such symptoms of latent (mildly marked) obsessive craving as mental stress, irritability, poor sleep. During the entire basic course of treatment (2 to 3 weeks), the patients remained well-balanced, calm, enjoyed normal appetite and sleep. As a result of suppressing the craving for alcohol, the patients at the 1st and 2nd stages of alcoholism, when the symptoms of encephalopathy of alcoholic etiology had not yet set in, begin, as a rule, to critically assess the causes that led them to heavy drinking, repent and show the wish to recover.

When taking, on the doctor's prescription, 30 to 50 g of the alcoholic drink to which they are used 1 to 2 weeks after the beginning of treatment, all the patients remark on the subjective changes of the smell and taste of alcohol. The smell becomes repulsive and, in combination with the insipid, bitterish or metal aftertaste, this suppresses the wish to continue the use of alcohol.

Some 20 to 30 minutes after the intake of a provoking dose of alcohol, a state of intoxication set in in the patients, and their symptoms got out of all proportion with the small dose taken. At first the patients noted the subjective sensation of a large dose (10 to 15 times larger than what they actually took). Then disphoria set in, despondency which reached in half of them the state of melancholia. About 60 percent of the patients had headache; there was no sense of physical and mental relaxation. The patients sought privacy and went to bed. Objectively, a mild hyperemia of the face was observed (20 to 25 minutes after the intake of the above-mentioned dose), torpidity, irritability, which in response to excessive attention developed into viciousness. The breathing and pulse rates somewhat increased. Arterial pressure went up by 20 to 30 mm Hg. Some 30 to 40 minutes later, speech articulation became disordered, instability, shakiness on walking was observed, movement became uncoordinated, the muscular tonus increased, slight tremer of the fingers and sweatiness of the palms was observed.

However the patients' general somatic condition remained good. A physical examination, including electrocardiography, did not reveal any new pathology. Nor were any pathological changes observed by blood analysis and in kidney and liver tests.

Intoxication passed away after 2 to 4 hours, and the normal sense of wellbeing was restored after 12 to 24 hours. During repeated attempts at provocation, the patients, as a rule, flatly refused alcohol, unwilling to undergo for a second time the unpleasant and grave condition.

Treatment in hospital for 2 to 3 weeks, followed by 2 to 3 months of out-patient treatment under medical supervision, ensured a stable remission in the majority of the patients, which lasted 1 to 2 years, mostly 1 to 1.5 years. Further on under the influence of emotional stress, a conflict situation, or under the influence of their immediate environment, persons who had taken a course of treatment with the present composition may gradually develop a craving for alcohol again. Therefor, in order to prevent this, it is advisable to repeat a course of treatment with the present composition after a period of 1 to 2 years.

The best results in regard of the duration of remission are achieved in patients with the 1st and 2nd stages of the disease. The mental instability and abulia characteristic of patients at the 3rd stage reduce the hope of complete recovery. However, even in the case of failure of remission, there is no relapse of the obsessive craving for alcohol, nor does dipsomania occur, as characteristic of treatment with other preparations (Antabuse and its analogues, Apomorphine and its analogues, etc.). The craving for alcohol in patients treated with Antabuse (group 2) and Apomorphine (group 3) is not removed (in contrast with using the present composition), but it is merely suppressed by fear of death (group 2) or the vomiting reflex (group 3).

For comparing the results of treatment in the three groups regarding the stability of the curative effect, Table 4 furnishes data on readmission to the hospital of earlier treated alcoholics.

Table 4

| Groups of patients 1 | Number of re-admissions to hospital (persons/percentage) | | | | Total of repeatedly treated patients (persons %) 6 |
|---|---|---|---|---|---|
| | after 1-2 years 2 | after 2nd year 3 | after 3rd year 4 | after 4 Years 5 | |
| 1st, treatment with present composition | 47/23.5 | 8/4 | 8/4 | — | 63/31.5 |
| 2nd, treatment with Antabuse | 109/54.5 | 24/12 | — | — | 133/66.5 |
| 3rd, treatment with Apomorphine | 151/75.5 | 18/9 | — | — | 169/84.5 |

Note:
1. Each group had 200 patients.
2. The Table indicates only those patients in whom failure of the remission was fraught with a relapse of alcoholism.

As the Table shows, the failure of remission in the first year after treatment in group 2 occurred approximately 2.3 times, and in group 3, about 3.2 times more frequently than in group 1, where the present composition was used. On the whole, in a period of four and a half years, the number of patients given repeated treatment in group 2 was about 2.1 times, and in group 3, about 2.7 times higher than in group 1.

The duration of remissions, assessed by the time period between the end of a course of hospital treatment and the first recorded use of alcohol, was the longest also in the patients of group 1 (see Table 5).

Table 5.

| Duration of remission, months | Duration of Remission Following Hospital Treatment | | |
|---|---|---|---|
| | Number of relapses according to groups | | |
| | 1 | 2 | 3 |
| 3 | — | 13 | 15 |
| 6 | 8 | 16 | 20 |
| 6 | 10 | 28 | 54 |
| 12 | 29 | 52 | 62 |
| Total for 1st year | 47 | 109 | 151 |
| 18 | 34 | 30 | 21 |
| 21 | 20 | 22 | 10 |
| 24 | 22 | 17 | 18 |
| Sum total for 2 years | 123 | 178 | 200 |
| 30 | 21 | 8 | — |
| 36 (3 years) | 19 | 9 | — |
| 42 | 16 | 2 | — |
| 48 (4 years) | 11 | 3 | — |
| 54 (4.5 years) | 10 | — | — |
| Total | 200 | 200 | 200 |

As the table shows, relapses occurred in 100% of cases among the patients of group 3 (controls) irrespective of the stage of the disease, towards the end of the second year from the end of tratment, while in the patients of group 2 (control), this picture was observed towards the end of the fourth year from the end of treatment, and in group 1 repeated use of alcohol (after treatment) is possible during the entire period of observation.

A comparison of the data in Tables 4 and 5 shows that a repeated course of treatment in the clinical hospital for relapses of the disease within two years was necessary for patients of group 1 in 44.7 percent of the cases (55 patients out of 123), for patients of group 2, 74.7 percent of the cases (133 out of 178), and for patients of group 3, in 84.5 percent of the cases (169 out of 200). These data confirm the high stability and duration of the curative effect reached when using the proposed preparation, compared to Antabuse and Apomorphine.

It should be noted, that rapid (within 2 to 3 weeks) normalization of the mental and physiological status of alcoholic patients, reached when using the present composition, excludes disintoxication theraby and the need for psycholeptic remedies, thereby removing the danger of the onset of medicamental narcomania induced by psycholeptics (Seduxen, Elenium, Meprobamate) and of polynarcomanias.

The active ingredient of the present composition $\omega$-(3'-phenylpyrrolidy-1')-6-propionyl benzo-1,4-dioxan hydrochloride, may be obtained in the following way.

3-phenylpyrrolidine is dissolved in alcohol, acidified with an alcoholic solution of hydrogen chloride, then 6-acetyl benzo-1,4-dioxan and paraform are added, and the mixture is boiled at a temperature of 60 to 120° C. in a flask with a reflux condenser for 4 to 6 hours. The alcohol is distilled off, the remnant is diluted with water. Then, the unreacted 6-acetyl benzo-1,4-dioxan is extracted from the reaction mixture with diethyl ether and regenerated.

Following extraction, the remnant is alkalized, and the base of $\omega$-(3'-phenylpyrrolidyl-1')-6-propionyl benzo-1,4-dioxan, formed in the process, is extracted with diethyl ether, after which the united ether extractions are dried with roasted magnesium (or sodium) sulfate, the solvent is distilled off, and the remnant is recrystallized from the diethyl ether. The obtained crystalline base is white in color or white with a faint cream tint, and its melting point is 64–66° C.

This base is dissolved in acetone, an alcoholic solution of hydrogen chloride is added to the solution while stirring and cooling to the solution while stirring and cooling to a temperature of 0 to 5° C. to reach pH=5.0. The precipitated end product is filtered off, dried at a temperature of 50° to 60° C. and recrystallized from ethyl alcohol acidified with hydrogen chloride. The yield of the end product comes to 50 to 60% by weight calculated with respect to 3 -phenylpyrrolidone. The content of pure ω -(3 '-phenylpyrrolidyl-1')-6 -propionyl benzo-1,4-dioxan hydrochloride in the end product is at least 99% by weight. The melting point of the end is 137 to 142° C. (within 2° C. for each test).

The medicinal forms of the present composition are prepared by standard methods.

No contra-indications to the use of the composition have been revealed.

Recommended single doses:

for oral administration, 0.015 to 0.045 g (single) and 0.180 g (daily);

for parenteral administration by subcutaneous or intramuscular injections, 2 to 3 ml of a 1% solution or a 1 to 3 ml of a 1.5% solution, but, as a rule, not more than 0.045 g per injection and not more than 0.120 g daily.

What is claimed is:

1. A composition for the treatment of alcoholism, comprising an effective amount for reducing a craving for alcohol and restoring normal body function of the active ingredient: ω-(3'-phenylpyrrolidyl-1')-6 -propionyl benzo-1,4-dioxan hydrochloride, of the following formula:

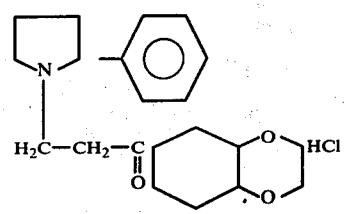

and a pharmaceutically acceptable carrier for said active ingredient.

2. A composition as claimed in claim 1, comprising as said pharmaceutically acceptable carrier a filler for tablets, selected from the group consisting of sodium chloride, starch, saccharose and lactose.

3. A composition as claimed in claim 2, comprising 0.015 to 0.030 g of said active ingredient per tablet.

4. A composition as claimed in claim 1, wherein said pharmaceutically acceptable carrier is a solvent comprising a 0.01 to 0.001 N hydrogen chloride solution in apyrogenic distilled water.

5. A composition as claimed in claim 4, comprising said active ingredient in a concentration of 1.0 to 1.5% by weight.

6. A method of treating alcoholism comprising administering an effective amount of the composition of claim 1 for reducing a craving for alcohol and restoring normal body function.

7. A method of treating alcoholism comprising orally administering the composition of claim 2, in an amount of from 0.015 to 0.045 g. per single dose and 0.180 g. daily.

8. A method of treating alcoholism comprising administering by subcutaneous or intramuscular injection the composition of claim 4, in an amount to provide a dose of from 0.015 to 0.045 g. of said active ingredient per injection and not more than 0.120 gram daily.

* * * * *

UNITED STATES PATENT OFFICE
CERTIFICATE OF CORRECTION

Patent No. 4,144,348          Dated March 13, 1979

Inventor(s) Irina N. Pyatnitskaya, et al

It is certified that error appears in the above-identified patent and that said Letters Patent are hereby corrected as shown below:

Column 1, line 7: after "composition" insert --and method--.

Column 2, line 38: "grous" should be --groups--.

Column 6, line 25: "tratment" should be --treatment--.

line 44: "theraby" should be --therapy--.

line 51: "'-phenylpyrrolidy" should be

--'-phenylpyrrolidyl--.

Signed and Sealed this

Eighteenth Day of September 1979

[SEAL]

Attest:

LUTRELLE F. PARKER
Attesting Officer      Acting Commissioner of Patents and Trademarks